(12) United States Patent
Fitzgerald (10) Patent No.: US 7,285,110 B2
(45) Date of Patent: Oct. 23, 2007

(54) RETRACTABLE HYPODERMIC SAFETY SYRINGE

(75) Inventor: Lisa Marie Fitzgerald, Sarasota, FL (US)

(73) Assignee: P. Rowan Smith, Jr., Houston, TX (US)

( * ) Notice: Subject to any disclaimer, the term of this patent is extended or adjusted under 35 U.S.C. 154(b) by 315 days.

(21) Appl. No.: 10/457,948

(22) Filed: Jun. 10, 2003

(65) Prior Publication Data

US 2004/0254529 A1 Dec. 16, 2004

(51) Int. Cl.
 *A61M 5/00* (2006.01)
(52) U.S. Cl. ...................... 604/110; 128/919
(58) Field of Classification Search ............ 604/110, 604/195
See application file for complete search history.

(56) References Cited

U.S. PATENT DOCUMENTS

| | | |
|---|---|---|
| 858,025 A | 6/1907 | Reese |
| 1,692,047 A | 11/1928 | Moore |
| 2,661,740 A | 12/1953 | Hickey |
| 3,206,073 A | 9/1965 | Scislowicz |
| D204,670 S | 5/1966 | Gilson |
| 3,595,230 A | 7/1971 | Suyeoka et al. |
| 3,706,106 A | 12/1972 | Leopoldi |
| 3,812,841 A | 5/1974 | Isacson |
| 3,906,626 A | 9/1975 | Riuli |
| 4,026,287 A | 5/1977 | Haller |
| 4,123,091 A | 10/1978 | Cosentino et al. |
| 4,170,993 A | 10/1979 | Alvarez |
| D259,278 S | 5/1981 | McCaw et al. |
| 4,361,147 A | 11/1982 | Aslanian et al. |
| 4,409,990 A | 10/1983 | Mileikowsky |
| 4,412,832 A | 11/1983 | Kling et al. |
| 4,429,856 A | 2/1984 | Jackson |
| 4,436,125 A | 3/1984 | Blenkush |
| 4,441,621 A | 4/1984 | Matakura et al. |
| 4,506,691 A | 3/1985 | Tseo |
| 4,507,117 A | 3/1985 | Vining |
| 4,518,385 A | 5/1985 | Lindmayer et al. |
| 4,588,402 A | 5/1986 | Igari et al. |
| 4,602,433 A | 7/1986 | Whiting |
| 4,629,159 A | 12/1986 | Wellenstam |
| 4,631,829 A | 12/1986 | Schmidt et al. |
| 4,643,200 A | 2/1987 | Jennings, Jr. |
| 4,650,468 A | 3/1987 | Jennings, Jr. |
| 4,675,005 A | 6/1987 | Deluccia |
| 4,683,916 A | 8/1987 | Raines |

(Continued)

FOREIGN PATENT DOCUMENTS

EP 0347742 B1 9/1992

(Continued)

OTHER PUBLICATIONS

Retrack USA, Inc., StatTrak™ Safety Syringe, 6 pages (1997).

(Continued)

*Primary Examiner*—LoAn H. Thanh
(74) *Attorney, Agent, or Firm*—Richard L. Moseley (57) ABSTRACT

A retractable hypodermic safety syringe device is provided for encapsulating a needle after use to prevent accidental needlesticks. The retractable syringe device includes a syringe barrel having one or more locking tabs for securing a needle carrier. A hypodermic needle attached to the needle carrier. A plunger having a piston slideably mounted within the syringe body. Locking fingers on the needle carrier for receiving the plunger.

4 Claims, 6 Drawing Sheets

U.S. PATENT DOCUMENTS

| | | | |
|---|---|---|---|
| 4,687,472 A | 8/1987 | Gross | |
| 4,692,156 A | 9/1987 | Haller | |
| 4,699,356 A | 10/1987 | Hargrove et al. | |
| 4,710,170 A | 12/1987 | Haber | |
| 4,735,202 A | 4/1988 | Williams | |
| 4,745,950 A | 5/1988 | Mathieu | |
| 4,747,830 A | 5/1988 | Gloyer | |
| 4,747,831 A | 5/1988 | Kulli | |
| 4,752,292 A | 6/1988 | Lopez et al. | |
| 4,758,231 A | 7/1988 | Haber et al. | |
| 4,790,822 A * | 12/1988 | Haining | 604/110 |
| 4,790,832 A | 12/1988 | Lopez et al. | |
| D300,361 S | 3/1989 | Tokarz | |
| 4,832,696 A | 5/1989 | Luther et al. | |
| 4,850,961 A | 7/1989 | Wanderer et al. | |
| 4,850,968 A | 7/1989 | Romano | |
| 4,883,471 A | 11/1989 | Braginetz et al. | |
| 4,888,002 A | 12/1989 | Braginetz et al. | |
| 4,892,107 A | 1/1990 | Haber | |
| 4,900,307 A | 2/1990 | Kulli | |
| 4,909,793 A | 3/1990 | Vining et al. | |
| 4,919,129 A | 4/1990 | Weber, Jr. et al. | |
| 4,919,652 A | 4/1990 | Alter et al. | |
| 4,931,040 A | 6/1990 | Haber et al. | |
| 4,944,725 A | 7/1990 | McDonald | |
| 4,950,241 A | 8/1990 | Ranford | |
| 4,950,251 A | 8/1990 | Haining | |
| 4,950,252 A | 8/1990 | Luther et al. | |
| 4,957,483 A | 9/1990 | Gonser et al. | |
| 4,973,316 A | 11/1990 | Dysarz | |
| D313,277 S | 12/1990 | Haining | |
| 5,019,049 A | 5/1991 | Haining | |
| 5,024,660 A | 6/1991 | McNaughton | |
| 5,025,520 A | 6/1991 | Watkins | |
| 5,026,354 A | 6/1991 | Kocses | |
| 5,035,695 A | 7/1991 | Weber, Jr. et al. | |
| 5,038,794 A | 8/1991 | Van Valkenburg | |
| 5,041,087 A | 8/1991 | Loo et al. | |
| 5,049,128 A | 9/1991 | Duquette | |
| 5,053,010 A | 10/1991 | McGary et al. | |
| 5,070,885 A | 12/1991 | Bonaldo | |
| 5,071,418 A | 12/1991 | Rosenbaum | |
| 5,071,426 A | 12/1991 | Dolgin et al. | |
| 5,099,578 A | 3/1992 | Jan | |
| 5,102,394 A | 4/1992 | Lasaitis et al. | |
| 5,112,316 A | 5/1992 | Venturini | |
| 5,120,311 A | 6/1992 | Sagstetter et al. | |
| 5,131,429 A | 7/1992 | Nixon | |
| 5,133,730 A | 7/1992 | Biro et al. | |
| 5,139,507 A | 8/1992 | Dolgin et al. | |
| 5,147,328 A | 9/1992 | Dragosits et al. | |
| 5,152,150 A | 10/1992 | Elliott, Jr. | |
| 5,152,750 A | 10/1992 | Haining | |
| 5,163,922 A | 11/1992 | McElveen, Jr. et al. | |
| 5,176,650 A | 1/1993 | Haining | |
| 5,180,370 A | 1/1993 | Gillespie | |
| 5,184,652 A | 2/1993 | Fan | |
| 5,188,599 A | 2/1993 | Botich et al. | |
| 5,195,985 A | 3/1993 | Hall | |
| 5,199,947 A | 4/1993 | Lopez et al. | |
| 5,201,719 A | 4/1993 | Collins et al. | |
| 5,201,748 A | 4/1993 | Newman et al. | |
| 5,207,696 A | 5/1993 | Matwijcow | |
| 5,211,638 A | 5/1993 | Dudar et al. | |
| 5,222,947 A | 6/1993 | D'Amico | |
| 5,242,423 A | 9/1993 | Goodsir et al. | |
| 5,244,465 A | 9/1993 | Michel | |
| 5,269,771 A | 12/1993 | Thomas et al. | |
| 5,273,254 A | 12/1993 | McNaughton et al. | |
| 5,277,402 A | 1/1994 | Szabo | |
| 5,279,853 A | 1/1994 | Occhiello et al. | |
| 5,297,776 A | 3/1994 | Dieringer | |
| 5,298,024 A | 3/1994 | Richmond | |
| 5,308,329 A * | 5/1994 | Mazur et al. | 604/110 |
| 5,330,493 A | 7/1994 | Haining | |
| 5,338,304 A | 8/1994 | Adams | |
| 5,342,323 A | 8/1994 | Haining | |
| 5,380,288 A | 1/1995 | Hart et al. | |
| 5,395,352 A | 3/1995 | Penny | |
| 5,401,245 A | 3/1995 | Haining | |
| 5,405,331 A | 4/1995 | Behnke et al. | |
| 5,441,487 A | 8/1995 | Vedder | |
| 5,445,620 A | 8/1995 | Haber et al. | |
| 5,453,093 A | 9/1995 | Haining | |
| 5,484,414 A | 1/1996 | Pace | |
| 5,527,306 A | 6/1996 | Haining | |
| 5,533,983 A | 7/1996 | Haining | |
| 5,556,409 A | 9/1996 | Haining | |
| 5,599,327 A | 2/1997 | Sugahara et al. | |
| 5,603,706 A | 2/1997 | Wyatt et al. | |
| 5,613,954 A | 3/1997 | Nelson et al. | |
| 5,709,669 A | 1/1998 | Haining | |
| 5,785,693 A | 7/1998 | Haining | |
| 5,885,257 A | 3/1999 | Badger | |

FOREIGN PATENT DOCUMENTS

| | | |
|---|---|---|
| EP | 0327061 B1 | 5/1993 |
| EP | 0402908 B1 | 5/1994 |
| EP | 0388137 B1 | 6/1994 |
| EP | 0392765 B1 | 6/1994 |
| EP | 0382190 B1 | 11/1995 |
| KR | 214990 | 8/1995 |
| SU | 0906563 | 2/1982 |
| WO | WO9100750 A1 | 1/1991 |
| WO | WO9218187 A1 | 10/1992 |
| WO | WO9221389 A1 | 12/1992 |
| WO | WO9617646 A1 | 6/1996 |

OTHER PUBLICATIONS

"Software helps sharpen syringe design," Design News, 3 pages (Aug. 16, 1993).

Boggs, Robert N., "Biopsy Instrument's Design Prevents Dangerous Reuse," Design News, pp. 83 & 85 (Aug. 16, 1993).

Bell, Rivian, "Luther Medical Reports second-quarter gains, appoints new chief financial officer," Business Wire, 2 pages (Jan. 12, 2003).

Donnelly, Jim, "Cinnaminson firm marketing an airbag for cars without one," Burlington County Times, 2 pages (Oct. 20, 1993).

Moskowitz, Dina, "Schapiro named president of U.S. Medical Instruments," Business Wire, 2 pages (Feb. 8, 1993).

Kazenelson, Deborah, "Origin Medsystems appeals injunction on new surgical device," Business Wire, 2 pages (Jan. 13, 1993).

McComb, Christen R., "Surgical Technologies plans new product launch," PR Newswire, 2 pages (Nov. 4, 1993).

Manning, Jeff, "Innovative Ziba designing a worldly future: Tokyo office opens, Chicago next," The Business Journal—Portland, vol. 10, Iss. 16, 3 pages (Jun. 14, 1993).

"Firm inks pact to raise $1 million for R&D of hypodermic needle disposal unit," Enterprise, vol. 22, Iss. 38, 1 page (Mar. 8, 1993).

"Nurses See Threat from Needle Sticks," National Underwriter [Property/Casualty/Employee Benefits], vol. 96, Iss. 35, 1 page (Aug. 31, 1992).

Bell, Rivian, "Luther Medical could gain from Critikon injunction against Becton Dickinson safety catheter," Business Wire, 2 pages (Jul. 27, 1993).

"Conical fittings with a 6% (Luer) taper for syringes, needles and certain other medical equipment—Part 1: General Requirements," ISO 594/1-1986(E), 7 pages (1986).

"Conical fittings with 6% (Luer) taper for syringes, needles and certain other medical equipment—Part 2: Lock fittings," ISO 594/2-1998(E), 11 pages (1998).

"Top Dental Products: Safety needle," 1 page (undated).
"AIDS Crisis Results in Development of Safer Dental Needle," Health Technology Systems, Inc., 6 pages (Nov. 22, 1991).
"Prevent accidental needle sticks," MPL Technologies, 1 page (1996).
"Anesthetic & Accessories from Septodont," Septodont, Inc., 2 pages (undated).

"Product catalog 1991," Septodont, Inc., cover and pp. 1-7 (1991).
"Merchandise Reference Catalog," Healthco International, Inc., p. 36-37 (1991).
"If a Disposable Is Available, Use It," DW Technology, Dental Products Report, p. 78 (May 1993).

* cited by examiner

RETRACTABLE HYPODERMIC SAFETY SYRINGE

CROSS-REFERENCE TO RELATED APPLICATIONS

Not applicable.

STATEMENTS REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention

The present invention relates to a retractable hypodermic safety syringe. In particular, the present invention relates to a safety syringe for completely encapsulating a needle after use to prevent accidental needlesticks or reuse of the needle.

2. Description of the Related Art

Healthcare workers in the United States suffer over a half million needlesticks each year. From these needlestick injuries healthcare workers contract HIV, become infected with hepatitis C and hepatitis B, and acquire such infectious diseases as tuberculosis, syphilis, malaria, herpes, diphtheria, gonorrhea, typhus and Rocky Mountain spotted fever.

Healthcare workers worldwide are concerned about accidental needlesticks resulting in life-threatening infections. Often, healthcare workers become patients after being injured by contaminated needles. These healthcare workers contract potentially deadly infections from needlestick injuries that are largely preventable.

Many methods and devices have been created to reduce accidental needlesticks by contaminated needles. An example of such a device is shown in U.S. Pat. No. 4,790,822. This patent discloses a retractable hypodermic safety syringe that retracts the used needle into the barrel of the syringe after use. A disadvantage of the design, however, was the expense and the difficulty of manufacture related to the molded internal parts of the syringe barrel, such as shoulders. Another disadvantage of this device was the inability to evacuate the entire contents of the cavity

BRIEF SUMMARY OF THE INVENTION

Briefly, the present invention provides an improved retractable hypodermic safety syringe that allows the needle to be retracted into the syringe cylinder after an injection has been given without the practitioner contacting the needle, thereby avoiding contamination by infectious agents. The retractable syringe device is simple and convenient to use. Additionally, the retractable syringe device is easy to manufacture because there are few internal parts molded to the inside of the syringe barrel. Moreover, the device includes locking and releasing tabs that provide a positive locking mechanism without the need for close tolerance snap fittings. Further, the retractable syringe device provides a means for evacuating the entire contents of the syringe barrel and needle carrier cavity.

The retractable syringe device includes a syringe cylinder, and a needle carrier for securing a hypodermic needle. A plunger snap coupling engages the needle carrier, allowing the needle carrier to be slid into the cylinder as the plunger is retracted to a locked position. As this snap coupling occurs, further pressure on the plunger also releases a set of positive locking tabs that secure the needle carrier to the syringe cylinder. This set of locking tabs insures that the needle carrier will not become dislodged during normal operation of loading and injecting medications.

BRIEF DESCRIPTION OF THE SEVERAL VIEWS OF THE DRAWINGS

A better understanding of the present invention can be obtained when the following detailed description of the preferred embodiment is considered in conjunction with the following drawings, in which.

DETAILED DESCRIPTION OF THE INVENTION

Figure 1:
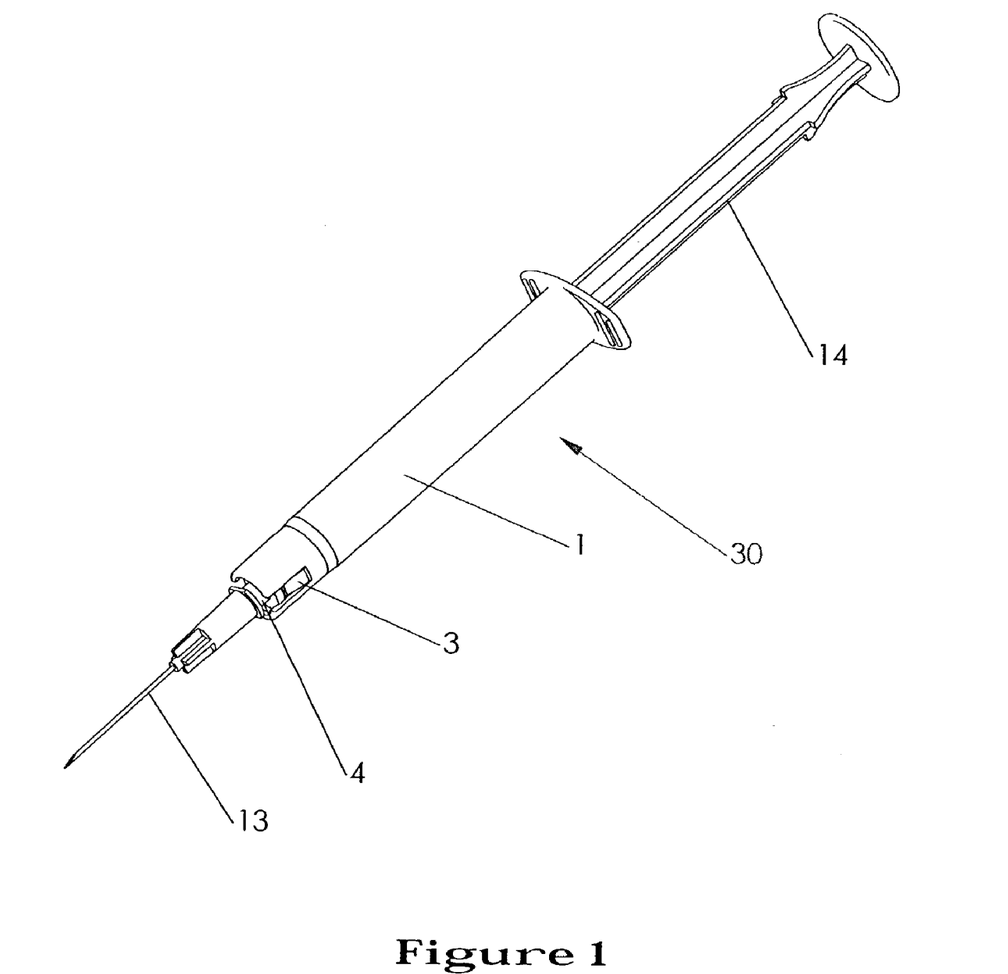
FIG. 1 is an elevational view of the retractable hypodermic safety syringe of the present invention.

A retractable hypodermic safety syringe device 30 according to the present invention is shown in FIG. 1 prior to use. The retractable syringe device 30 includes a syringe barrel or body 1 for holding injectable fluids. A plunger 14 is inserted at one end of the syringe barrel 1. The opposite end of the syringe barrel 1 includes a needle carrier 4 which receives a hypodermic needle 13 for injecting patients.

The syringe barrel 1 includes locking tabs 3 for securing the needle carrier 4 to the syringe body 1 prior to retraction of the needle 13 into the syringe body. In the preferred embodiment, the locking tabs 3 are molded into the wall of the syringe body 1. A notch 21 on the needle carrier 4 receives a lip portion 32 of the locking tabs 13 and secures the needle carrier 4 within the syringe barrel 1. The syringe barrel 1 also includes a lower body portion 23 for abutting the needle carrier 4 on a front surface 7. The combination of the locking tabs 3 and the lower body 23 works to retain the needle carrier 4 within the syringe barrel 1 during loading of the syringe and injecting of the fluid into a patient.

Figure 2:
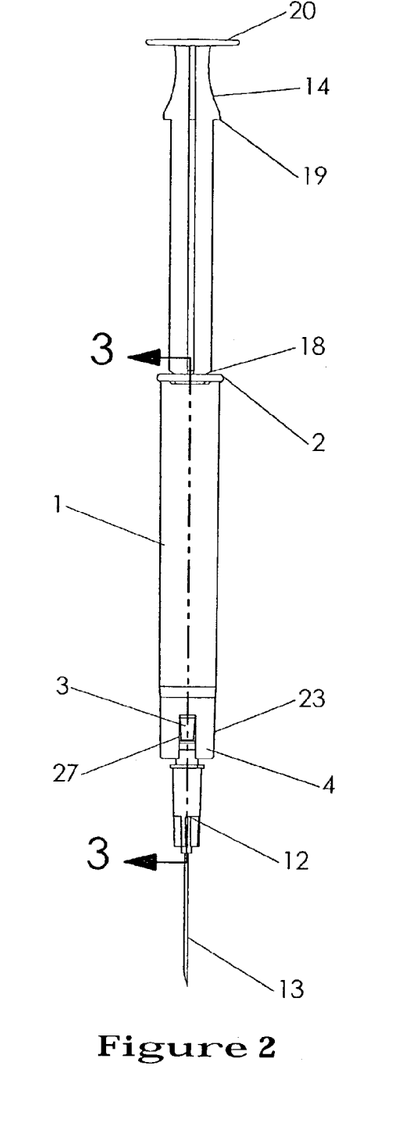
FIG. 2 is a side elevational view of the device in FIG. 1.
Figure 3:
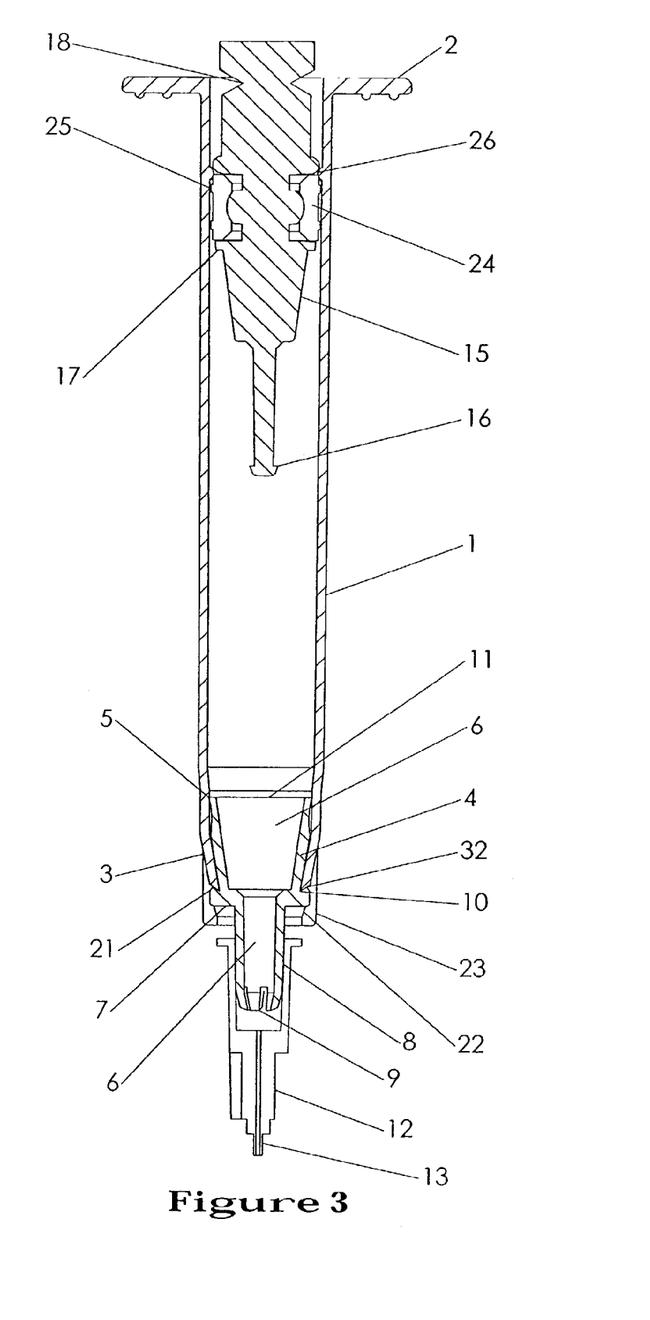
FIG. 3 is a side elevational view, partially in section, as viewed along line 3-3 of FIG. 2.

Referring to FIGS. 2 and 3, the retractable syringe device 30, is shown with the plunger 14 in the fully retracted position. The plunger 14 includes a piston 15 and a plunger snap 16 extending from the piston for engaging the needle carrier 4. Outward travel of the plunger 14 within the syringe barrel 1 is limited by a plunger seal interference ring 26 located on the interior of the syringe barrel 1. Typically, the syringe barrel is made from a mold which includes relief for the interference ring 26. A plunger seal 24 secured to the plunger 14 includes a plunger wiping ring 25 which contacts the interference ring 26 when the plunger 14 is extracted during loading of the syringe barrel.

The needle carrier 4 includes the notch 21 for receiving the locking tabs 3 to secure the needle carrier 4 to the syringe barrel 1. The needle carrier 4 also includes a carrier seal 5 sized to be in an interference fit with the inner wall on the syringe body 1. The carrier seal 5 prevents fluid from leaking out of the syringe barrel 1. Fingers 9 for receiving the plunger snap 16 extend from a cavity 6 of the needle carrier 4. The needle 13 includes a conical fitting 12 which is pressed and sealed onto a carrier conical fitting 8.

Figure 4:
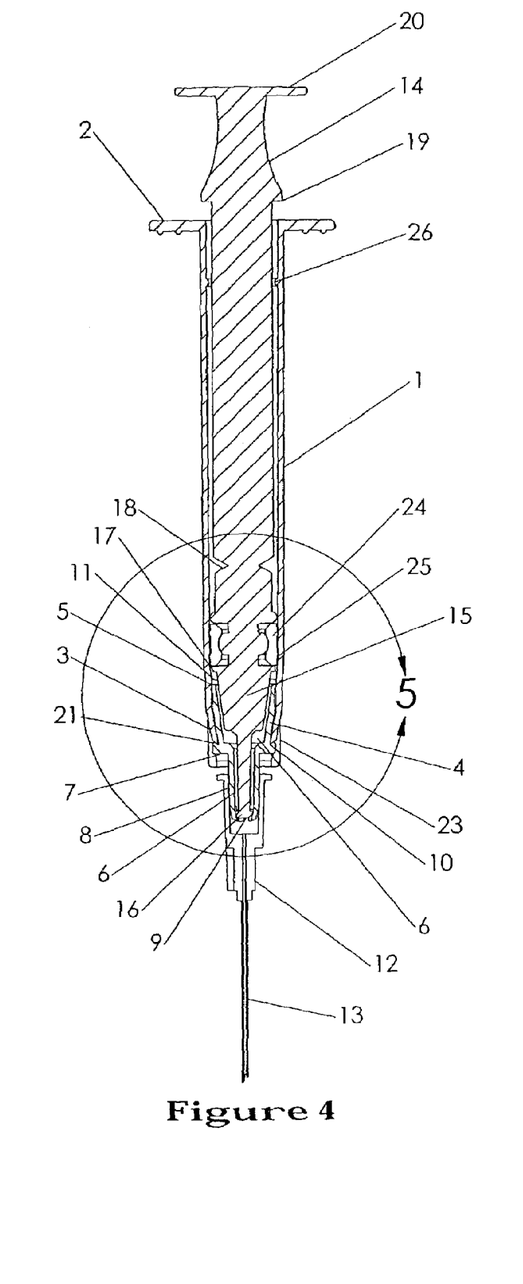
FIG. 4 is a side elevational view, partially in section, of the device in FIG. 1.
Figure 5:
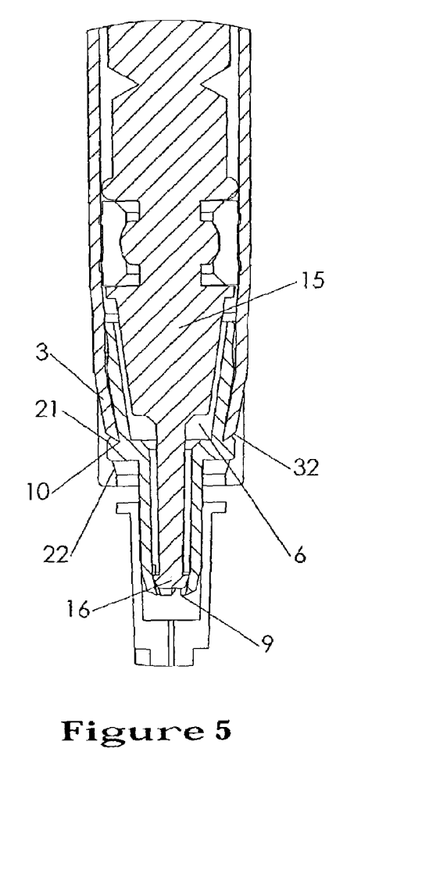
FIG. 5 is an expanded side elevational view, partially in section, of a portion of the device within circle 5 of FIG. 4.

Referring to FIGS. 4 and 5, the plunger 14 is into the syringe barrel 1 by means of a plunger grip 20 and a syringe body grip 2 until resistance is felt due to the contact of the snap 16 with the locking fingers 9. The resistance occurs when the load is ejected from the syringe and when the syringe is being loaded with fluid. Upon feeling the resistance, the user appreciates that the plunger snap 16 is almost engaged by the fingers 9 of the needle carrier 4. At this point the plunger piston 15 is moved into the geometrically matching cavity 6, which purges the load (or air, if in fill mode) from the cavity 6.

Figure 6:
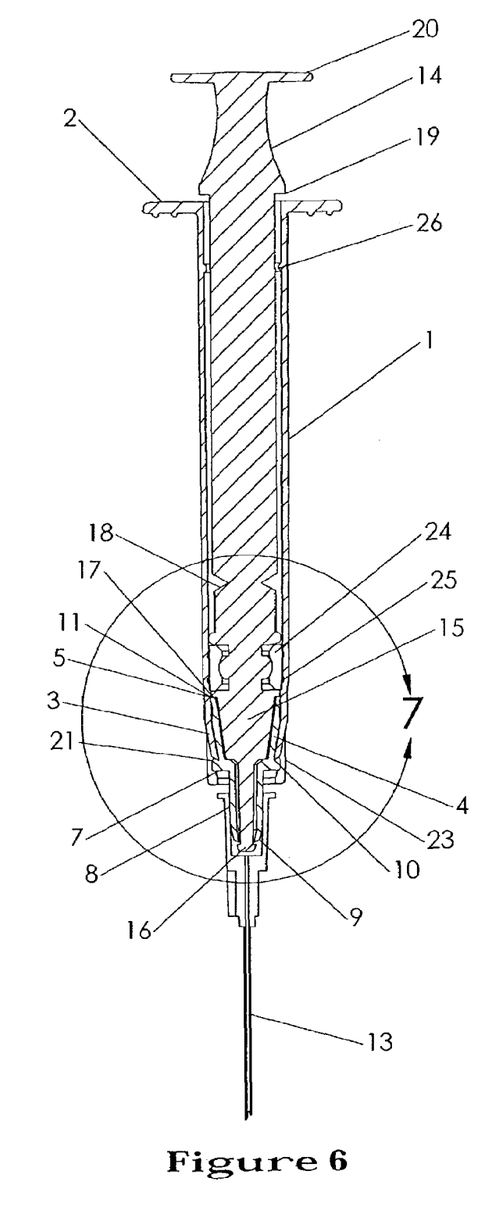
FIG. 6 is a side elevational view, partially in section, of the device in FIG. 1.
Figure 7:
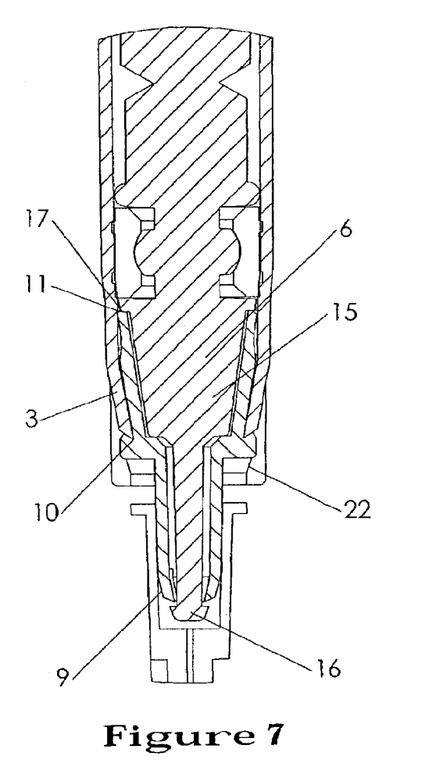
FIG. 7 is an expanded side elevational view, partially in section, of a portion of the device within circle 7 of FIG. 6.
Figure 8:
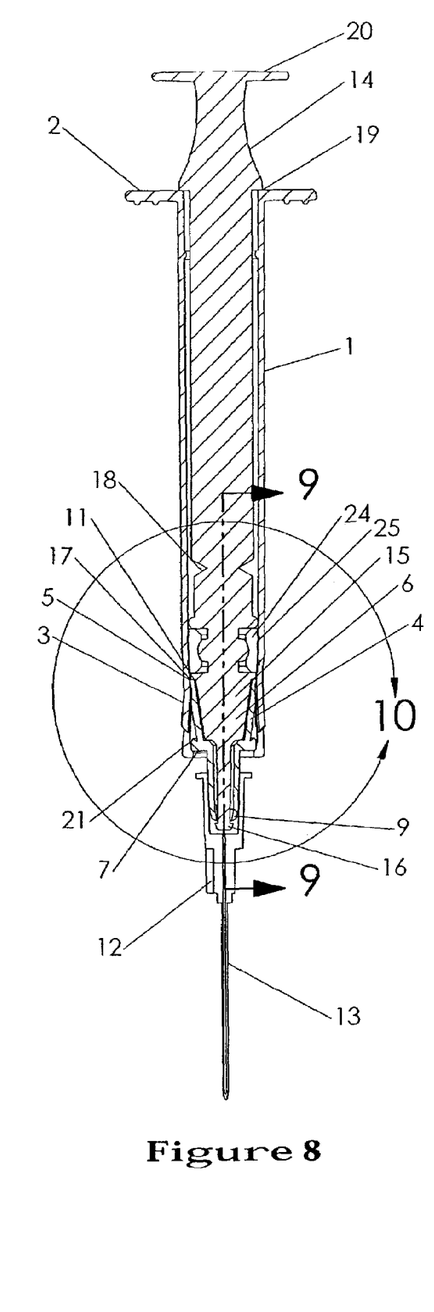
FIG. 8 is a side elevational view, partially in section, of the device in FIG. 1.
Figures 9, 10:
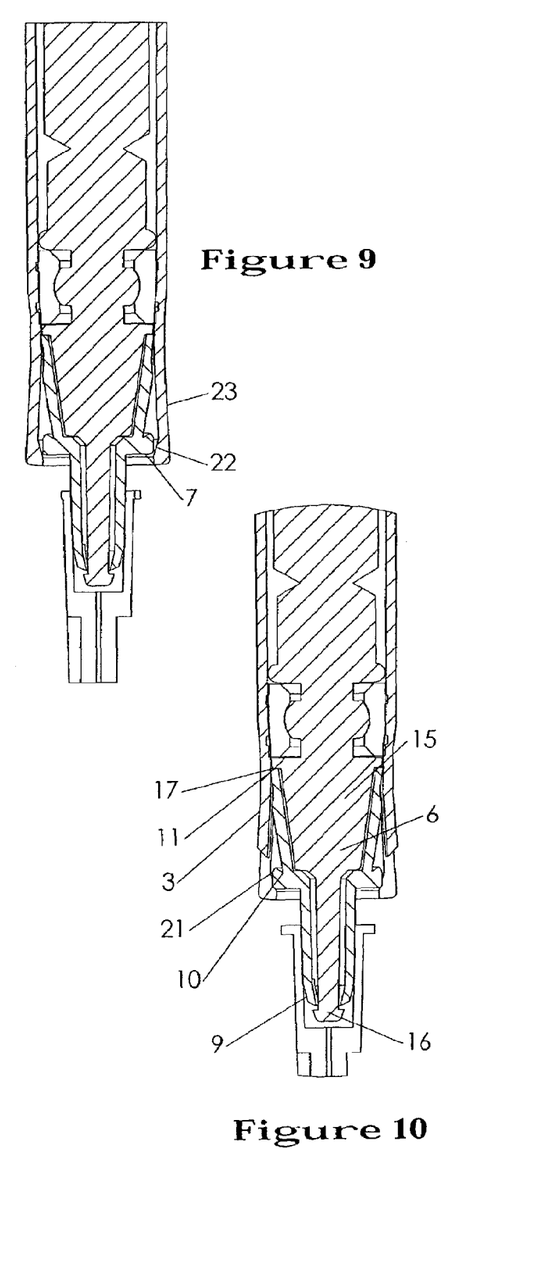
FIG. 9 is a side elevational view, partially in section, as viewed along line 9-9 of FIG. 8.
FIG. 10 is an expanded side elevational view, partially in section, of a portion of the device within circle 10 of FIG. 8.
Figures 11, 12, 13:
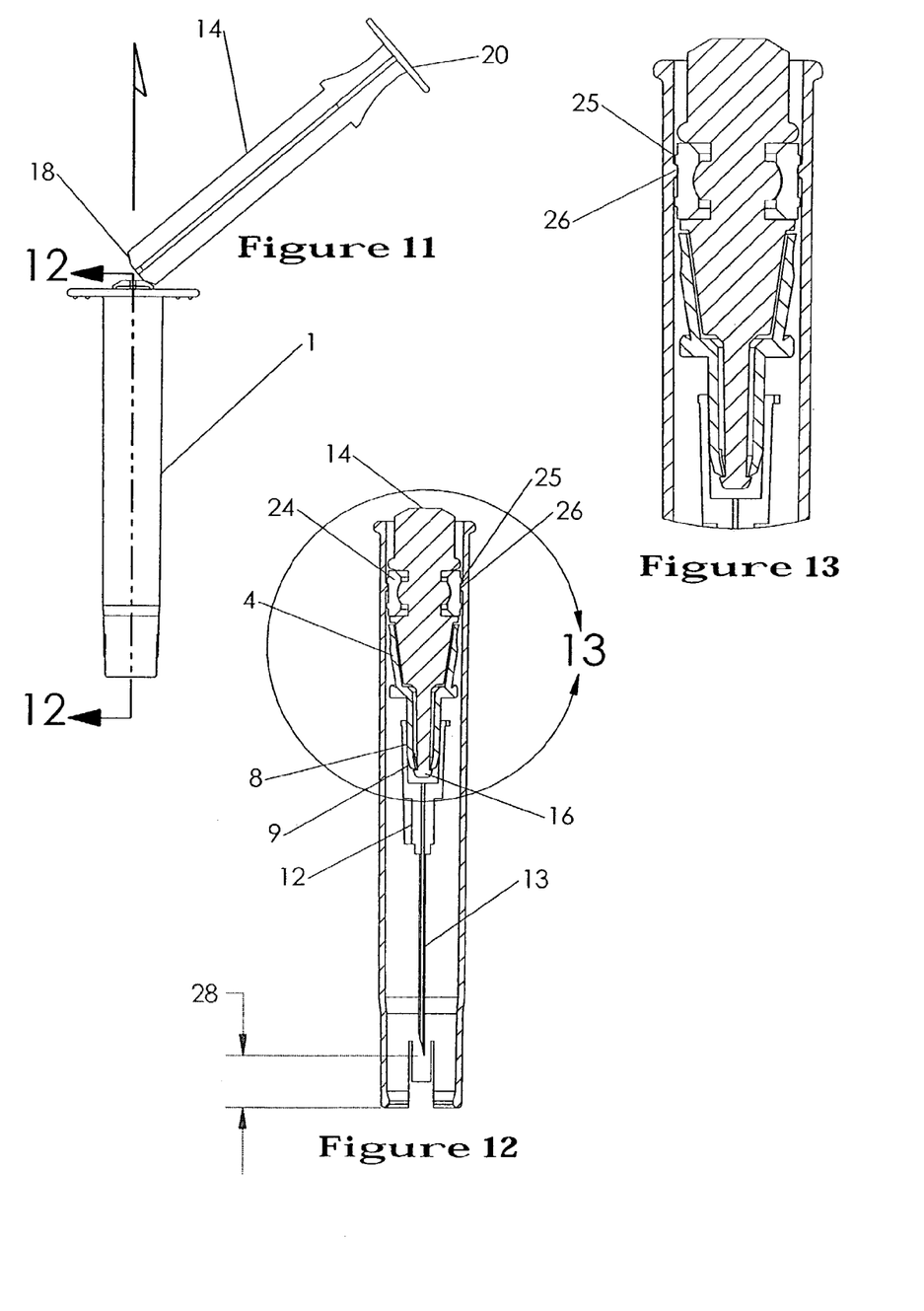
FIG. 11 is a side elevational view of the device in FIG. 1.
FIG. 12 is a side elevational view, partially in section, of the device in FIG. 11.
FIG. 13 is an expanded side elevational view, partially in section, of a portion of the device within circle 13 of FIG. 12.

As shown in FIGS. 6 and 7 when the injection is finished and it is desired to set the needle 13 to the safe position (as shown in FIG. 12) the user must apply sufficient pressure to the plunger grip 20 to spring the carrier locking fingers 9 open and allow the plunger snap 16 to pass through and lock behind the carrier locking fingers 9. As shown in FIGS. 8-10, as the user continues to apply pressure to the plunger grip 20, a plunger push surface 17 contacts a rear surface 11 of the needle carrier 4 until a plunger stop 19 on the plunger 14 contacts the syringe body grip 2.

At this point, the needle carrier 4 has moved sufficiently to allow the locking tabs 3 to release from the notch 10 of the needle carrier 4. The locking tabs 3 are sprung to the position shown in FIG. 10, returning to their normal "as molded," pre-loaded position. To insure the locking tabs 3 are ejected from the notch 10, a carrier tab ejection surface 21 on the needle carrier 4 is used to push the locking tabs 3 outward as the needle carrier 4 is pulled back by the plunger 14.

For the device to work properly, the force to slide the needle carrier 4 and release the locking tabs 3 must be greater than the snap mechanism comprised of the plunger snap 16 and the fingers 9. This insures that the locking tabs 3 do not disengage until the plunger grip 20 has had sufficient force applied to cause the snap engagement of the plunger snap 16 and fingers 9. The force required for releasing the tabs 3 is much greater than what is felt in normal filling and dispensing of the load. As a result, the locking tabs 3 will stay engaged until the user desires release of the needle carrier 4.

Referring to FIGS. 9 and 10, as the needle carrier 4 is pushed by the plunger 14, a carrier front surface 7 contacts a syringe body ramp 22 on the lower body portion 23, which causes the lower syringe body 23 to flex outward. The force required to cause the flex and allow travel of the needle carrier 4 is greater than the force required to engage the plunger snap 16 and the carrier locking fingers 9, thereby insuring the locking tabs 3 are held in place in the notch 10 until after this snap occurs. The deflection force of the lower syringe body 23, as shown in FIG. 9, is applied by the distortion strain of the circular cross section geometry, as relieved by a syringe body slot 27.

Referring to FIGS. 11-13, with locking tabs 3 disengaged, the plunger 14 can now be pulled to the fully retracted position by the plunger grip 20 until the plunger wiping ring 25 passes the plunger seal interference ring 26, indicating to the user the end of travel of the plunger 14. At this point the plunger 14 can be broken at a plunger break-off notch 18, leaving the plunger piston 15, plunger seal 24, needle carrier 4, and needle 13 inside the syringe body 1. This assembly is held in position by the plunger wiping ring 25 and the plunger seal interference ring 26. The needle 13 is recessed a distance 28 to protect the user from needlesticks.

I claim:

1. A retractable hypodermic safety syringe device comprising:
   a syringe barrel with a hollow interior and open on each end, said barrel having a distal end with an internal inwardly protruding ramp at said distal end;
   locking tabs molded into said distal end of said syringe barrel, each of said locking tabs having a lip protruding into said hollow interior;
   a needle carrier for securing a hypodermic needle, said carrier having a notch facing opposite said distal end for receiving said lip and having a front surface for contacting said ramp and a carrier tab ejection surface for contacting said locking tabs;
   a plunger slideably mounted with said syringe barrel;
   a piston secured to an end of said plunger, said piston having a snap extending therefrom;
   locking fingers on said needle carrier for receiving said snap and securing said needle carrier to said plunger, said fingers extending away from said hollow interior of said syringe barrel;
   said needle carrier being releasably secured in position at said distal end by the engagement of said lip with said notch;
   the distal end of said barrel being flexible outward by the contact of said front surface against said ramp to release said locking tabs from said notch and said locking tabs being held open by said carrier tab ejection surface as said needle carrier is retracted; and
   the force required to release said locking tabs being greater than the force required to engage said snap in said fingers such that said locking tabs cannot be released until said snap is engaged in said fingers.

2. The retractable hypodermic safety syringe device according to claim 1, further comprising a seal secured to said plunger for preventing fluid from leaking from said syringe barrel.

3. The retractable hypodermic safety syringe device according to claim 1, wherein said plunger includes a notch for fracturing said plunger.

4. The retractable hypodermic safety syringe device according to claim 1, wherein said barrel includes a body grip at the proximal end and said plunger includes a plunger stop near the proximal end which engages said body grip when said plunger is fully depressed.

* * * * *